(12) United States Patent
Shunori et al.

(10) Patent No.: US 10,457,907 B2
(45) Date of Patent: Oct. 29, 2019

(54) ELECTROCHEMICAL MEASUREMENT DEVICE

(71) Applicant: PANASONIC INTELLECTUAL PROPERTY MANAGEMENT CO., LTD., Osaka (JP)

(72) Inventors: Atsushi Shunori, Osaka (JP); Masahiro Yasumi, Osaka (JP); Makoto Takahashi, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 163 days.

(21) Appl. No.: 15/277,728

(22) Filed: Sep. 27, 2016

(65) Prior Publication Data

US 2017/0015971 A1    Jan. 19, 2017

Related U.S. Application Data

(63) Continuation of application No. PCT/JP2015/000852, filed on Feb. 23, 2015.

(30) Foreign Application Priority Data

Mar. 31, 2014 (JP) .................... 2014-071484

(51) Int. Cl.
*G01N 27/403* (2006.01)
*G01N 33/487* (2006.01)
(Continued)

(52) U.S. Cl.
CPC .......... *C12M 41/34* (2013.01); *C12M 41/36* (2013.01); *C12Q 1/02* (2013.01); *C12Q 1/04* (2013.01);
(Continued)

(58) Field of Classification Search
CPC .............. G01N 27/403; G01N 27/327; G01N 27/3272; G01N 27/3275; G01N 33/48728;
(Continued)

(56) References Cited

U.S. PATENT DOCUMENTS

| 4,571,292 A | 2/1986 | Liu et al. |
| 8,753,893 B2 * | 6/2014 | Liu ................... B01L 3/5025 422/50 |

(Continued)

FOREIGN PATENT DOCUMENTS

| CN | 101595381 A | 12/2009 |
| CN | 102449468 A | 5/2012 |

(Continued)

OTHER PUBLICATIONS

International Search Report and Written Opinion issued in International Patent Application No. PCT/JP2015/000852, dated May 19, 2015; with partial English translation.

(Continued)

*Primary Examiner* — Susan D Leong
(74) *Attorney, Agent, or Firm* — McDermott Will & Emery LLP

(57) ABSTRACT

An electrochemical measurement device includes: a base; a specimen placement portion disposed on the base, for placing a biological specimen; a first electrode disposed on the base and surrounding the specimen placement portion; and a first insulating layer covering the first electrode. The first insulating layer has a plurality of openings, and the first electrode has a plurality of first electrode exposed portions which are portions of the first electrode that are exposed from the openings of the first insulating layer.

20 Claims, 5 Drawing Sheets

(51) Int. Cl.
  *G01N 33/50* (2006.01)
  *C12M 1/34* (2006.01)
  *C12Q 1/04* (2006.01)
  *G01N 33/543* (2006.01)
  *C12Q 1/02* (2006.01)

(52) U.S. Cl.
  CPC ..... *G01N 27/403* (2013.01); *G01N 33/48728* (2013.01); *G01N 33/5005* (2013.01); *G01N 33/5438* (2013.01)

(58) Field of Classification Search
  CPC ................. G01N 33/48; G01N 33/487; G01N 33/48785; G01N 33/50; G01N 33/5005
  See application file for complete search history.

(56) References Cited

U.S. PATENT DOCUMENTS

| | | |
|---|---|---|
| 2004/0045839 A1 | 3/2004 | Thewes et al. |
| 2004/0110277 A1 | 6/2004 | Maeda |
| 2004/0214312 A1 | 10/2004 | Tyvoll et al. |
| 2006/0252111 A1 | 11/2006 | Tyvoll et al. |
| 2009/0145780 A1 | 6/2009 | Sasaki et al. |
| 2012/0137797 A1 | 6/2012 | Sawamura |
| 2012/0267260 A1 | 10/2012 | Dharia et al. |
| 2013/0287156 A1* | 10/2013 | Yazdanbod ............. G21B 1/00 376/137 |
| 2015/0233902 A1* | 8/2015 | Akagami ........... G01N 33/5302 435/7.1 |
| 2015/0260675 A1 | 9/2015 | Nakatani et al. |
| 2017/0218423 A1* | 8/2017 | Hiramoto ................ C12Q 1/02 |

FOREIGN PATENT DOCUMENTS

| | | |
|---|---|---|
| JP | 04-204244 A | 7/1992 |
| JP | 2002-122568 A | 4/2002 |
| JP | 2003-529771 A | 10/2003 |
| JP | 2004-333485 A | 11/2004 |
| JP | 2010-121948 A | 6/2010 |
| JP | 2013-094168 A | 5/2013 |
| WO | 01/75149 A2 | 10/2001 |
| WO | 01/75149 A | 10/2003 |
| WO | 03/087798 A1 | 10/2003 |
| WO | 2014/073195 A1 | 5/2014 |

OTHER PUBLICATIONS

Extended European Search Report issued in Application No. 15772658.9 dated Mar. 1, 2017.

Search Report issued in Chinese Patent Application No. 201580016591.4, dated Jul. 19, 2017; with partial English translation.

* cited by examiner

ELECTROCHEMICAL MEASUREMENT DEVICE

CROSS REFERENCE TO RELATED APPLICATIONS

This application is a U.S. continuation application of PCT International Patent Application Number PCT/JP2015/000852 filed Feb. 23, 2015, claiming the benefit of priority of Japanese Patent Application Number 2014-071484 filed on Mar. 31, 2014, the entire contents of which are hereby incorporated by reference.

TECHNICAL FIELD

The present disclosure relates to an electrochemical measurement device for a biological specimen, which is used in examination and analysis of activity states of biological specimens such as cells, such as fertilized ova, and tissue.

DESCRIPTION OF THE RELATED ART

Biological specimens such as cells, such as fertilized ova, and tissue are active in conveying various substances inward and outward. For example, cardiac muscle cells convey K ions, Na ions, Ca ions, etc., thus transmitting information using electrical signals and compounds and controlling pulsation of the heart. Furthermore, in a fertilized ovum, surrounding oxygen is taken into the cell through respiration, and segmentation occurs inside an ovarian follicle while consuming the oxygen that has been taken in. Methods for electrically measuring a physicochemical change of state occurring in the vicinity of a biological specimen while the specimen is held in an electrochemical measurement device are known as means for measuring the state of activity of such biological specimens. These are used as methods for conducting, using model cells, pharmacological testing of compounds which are candidates for new drugs, examining activity of a fertilized ovum, etc.

As a method for measuring respiratory activity of a fertilized ovum, there is a method in which a fertilized ovum is acquired using, for example, a micromanipulator or a micropipette, and electrochemical measurement of the oxygen concentration in the vicinity of the fertilized ovum is performed using a working electrode. Using this method enables the respiratory activity of a fertilized ovum to be measured.

Since the aforementioned electrochemical measurement method is configured on the basis of scanning electrochemical microscopy (SECM), it is necessary to perform operation to bring the working electrode of a probe to the vicinity of the biological specimen such as a fertilized ovum, for example. However, operability is an issue because of the need to manually operate the working electrode, and there is the problem that unevenness arises due to operator technique.

On the other hand, a planar-style fertilized ovum respiratory activity measurement apparatus in which minute working electrodes are provided on a base is known as a means for improving operability.

The fertilized ovum respiratory activity measurement apparatus is formed by providing electrodes on a base. The entirety of the base is insulated by being covered by silicon dioxide. Part of the silicon dioxide is removed to expose the electrodes. Three electrodes are provided. Furthermore, a well for embryo position regulating support is created in the base, and an inverted cone-shaped polydimethylsiloxane (PDMS) well is bonded to the base.

It should be noted that Japanese Unexamined Patent Application Publication No. 2002-122568 (Patent Literature 1) and Japanese Unexamined Patent Application Publication No. 2010-121948 (Patent Literature 2), for example, are known as background art related to the present disclosure.

SUMMARY

In a biological specimen such as a cell, activity causes physicochemical change in the surroundings. However, the change in the surroundings of the biological specimen caused by the activity is not uniform, and there are instances where there is a bias in a certain direction. For example, in a fertilized ovum, polarity is established in respiratory activity together with the advancement in the developmental stage, and thus a bias is created in the amount of oxygen consumed in the surrounding of the fertilized ovum. In other words, depending on the direction from the fertilized ovum, there are instances where the amount of respiration changes even for the same fertilized ovum. As such, in a conventional respiratory activity measuring apparatus, a plurality of working electrodes are disposed around the specimen in consideration of the bias in the physicochemical change in the surroundings caused by the activity of the biological specimen in the case where electrochemical measurement of the specimen is performed. Then, by measuring the measurement values from each of the working electrodes and calculating the average value or a sum total, the respiratory activity measuring apparatus is able to measure the average state of activity of the specimen by electrochemical measurement. However, the conventional respiratory activity measurement apparatus requires the same number of extraction wires as the working electrodes used in measuring. As such, the respiratory activity measurement apparatus has the problem that the number of extraction wires increases as the number of working electrodes increases.

The present disclosure is conceived in order to solve the aforementioned problem and has as an object to provide an electrochemical measurement device which measures, using a plurality of working electrodes, a physicochemical change of state in oxygen concentration, etc., in the surroundings of a specimen, and has a small number of extraction wires.

In order to achieve the aforementioned object, an electrochemical measurement device for a biological specimen according to the present disclosure includes: a base; a specimen placement portion disposed on the base, for placing a biological specimen; a first electrode disposed on the base and surrounding the specimen placement portion; and a first insulating layer covering the first electrode.

The first insulating layer has a plurality of openings, and the first electrode has a plurality of first electrode exposed portions which are portions of the first electrode that are exposed from the openings of the first insulating layer.

An electrochemical measurement device for a biological specimen, according to the present disclosure includes a plurality of first electrode exposed portions provided in an electrode disposed on a base, and exposed from an insulating layer, at positions that are equidistant from a specimen placement portion. By having such a configuration, the electrochemical measurement device does not require respective extraction electrodes to be connected to the electrode exposed portions, that is, an electrochemical measurement device having a small number of extraction wires can be realized.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

DETAILED DESCRIPTION OF THE EMBODIMENTS

Hereinafter, an electrochemical measurement device according to embodiments of the present disclosure will be described in detail using the drawings. It should be noted that each of the subsequently-described exemplary embodiments show a specific preferred example of the present disclosure. Therefore, numerical values, shapes, materials, structural components, the arrangement and connection of the structural components, etc. shown in the following embodiments are mere examples, and are not intended to limit the scope of the present disclosure. Furthermore, among the structural components in the following embodiments, components not recited in any one of the independent claims which indicate the broadest concepts of the present disclosure are described as arbitrary structural components.

Furthermore, the respective figures are schematic diagrams and are not necessarily precise illustrations. Furthermore, in the respective figures, substantially identical components are assigned the same reference signs, and overlapping description is omitted or simplified.

Embodiment 1

Figure 1:
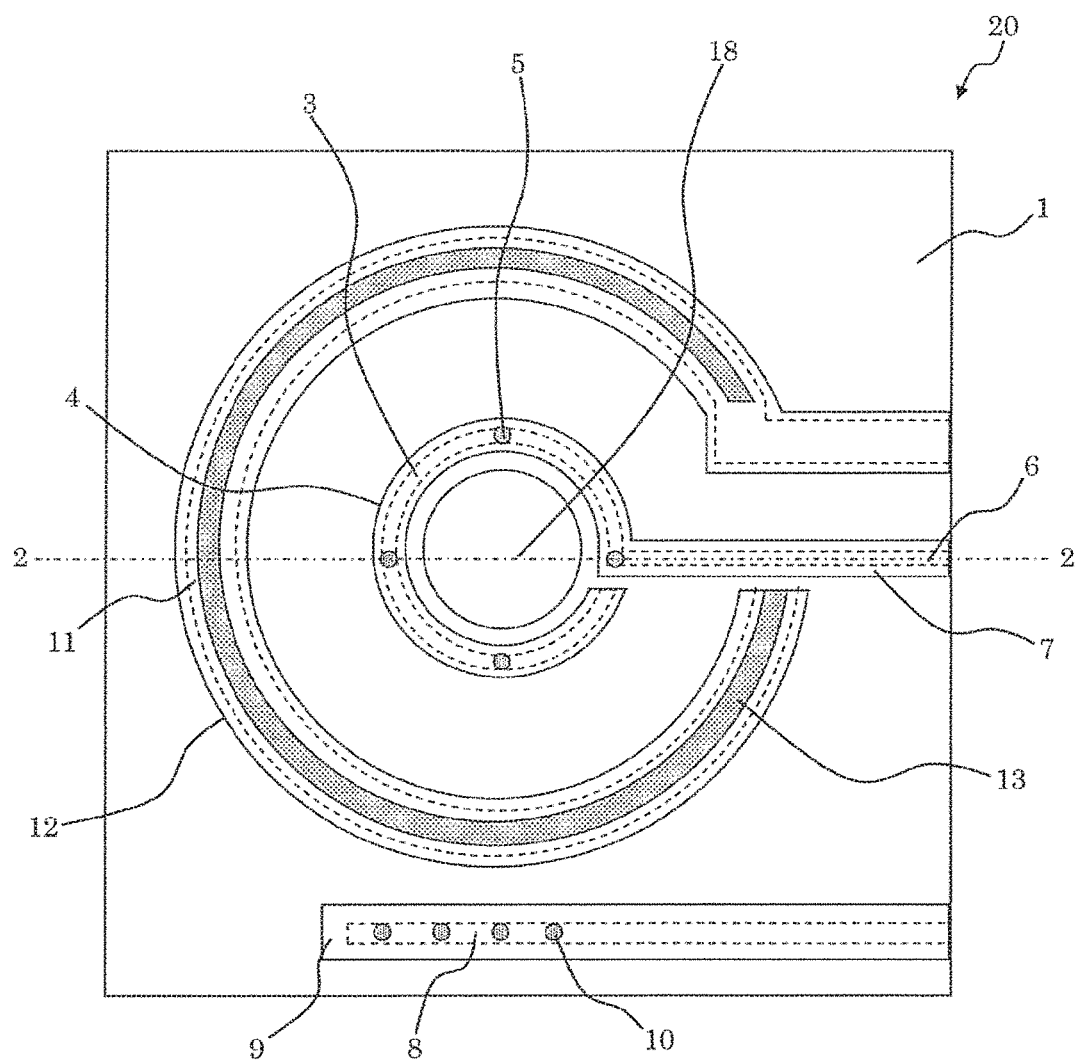
FIG. 1 is a top view of an electrochemical measurement device for a biological specimen in Embodiment 1.
Figure 2:
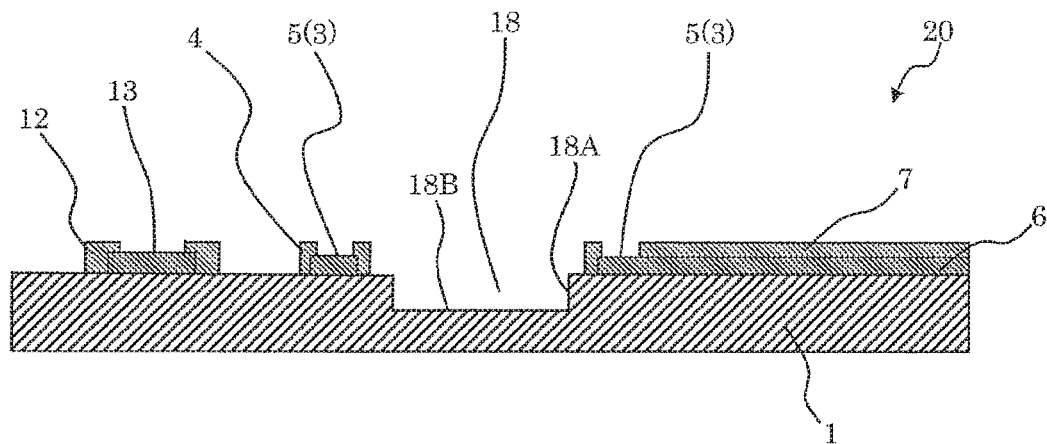
FIG. 2 is a cross-sectional view of an electrochemical measurement device for a biological specimen in Embodiment 1.

FIG. 1 is a top view schematically illustrating electrochemical measurement device 20 for a biological specimen in this embodiment. FIG. 2 is a cross-sectional view of electrochemical measurement device 20 for a biological specimen taken at line 2-2 in FIG. 1.

Electrochemical measurement device 20 for a biological specimen includes base 1, specimen placement portion 18 provided on base 1 and on which a biological specimen is placed, first electrode 3 provided on base 1 and surrounding specimen placement portion 18, and first insulating layer 4 covering first electrode 3.

First insulating layer 4 has a plurality of openings, and first electrode 3 includes a plurality of first electrode exposed portions 5 which are portions of first electrode 3 that are exposed from the openings of first insulating layer 4.

By having such a configuration, the electrochemical measurement device does not require respective extraction electrodes to be connected to the electrode exposed portions, that is, the number of extraction wires can be reduced.

Base 1 is formed of, for example, glass, resin, silicon, or ceramics.

Specimen placement portion 18 is a bottomed hole, that is, a recess that is provided in the top face of base 1. Specimen placement portion 18 is, for example, a column-shaped or polygonal column-shaped hole. In this embodiment, the diameter of specimen placement portion 18 is, for example, 200 μm. The diameter of specimen placement portion 18 is a value determined according to the size of the biological specimen. Furthermore, the depth of specimen placement portion 18 is, for example, 80 μm. The depth of specimen placement portion 18 is preferably less than or equal to half the height of the biological specimen. By setting the depth of specimen placement portion 18 to less than or equal to half the height of the biological specimen, the biological specimen is exposed from specimen placement portion 18, thus facilitating the detection of a physicochemical change of state in oxygen concentration, etc., by first electrode exposed portions 5. However, the depth of specimen placement portion 18 can be freely set in advance in accordance with the size of the biological specimen, and is not limited to being less than or equal to half the height of the biological specimen.

Furthermore, wall face 18A of specimen placement portion 18 and bottom face 18B of specimen placement portion 18 are preferably subjected to hydrophilic treatment. By making wall face 18A and bottom face 18B of specimen placement portion 18 hydrophilic, a solution can be poured into specimen placement portion 18 with ease, and retention of bubbles, etc. can be suppressed. The hydrophilic treatment of wall face 18A and bottom face 18B can be performed by ashing, for example.

Figure 3:
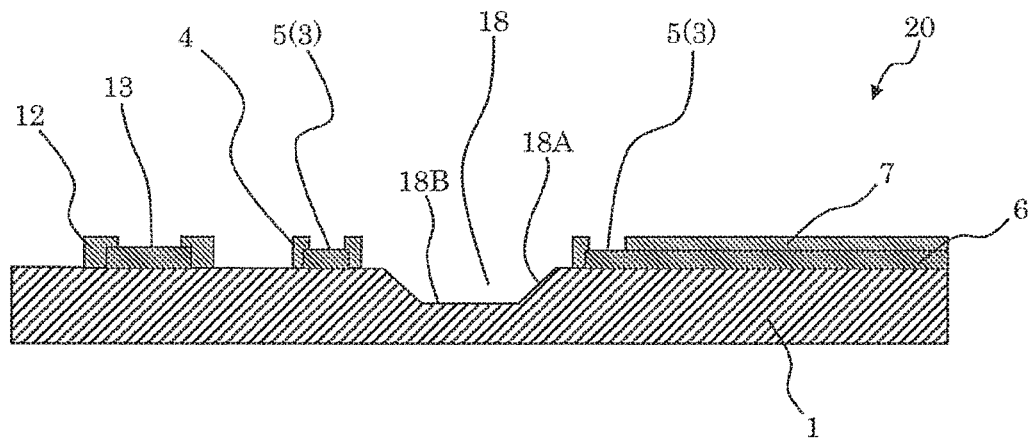
FIG. 3 is a cross-sectional view of another example of an electrochemical measurement device for a biological specimen in Embodiment 1.
Figure 4:
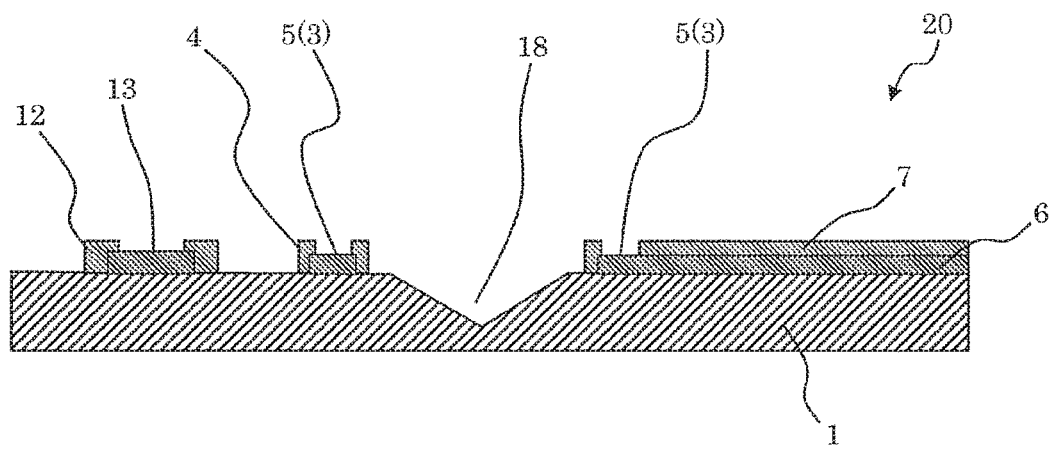
FIG. 4 is a cross-sectional view of another example of an electrochemical measurement device for a biological specimen in Embodiment 1.
Figure 5:
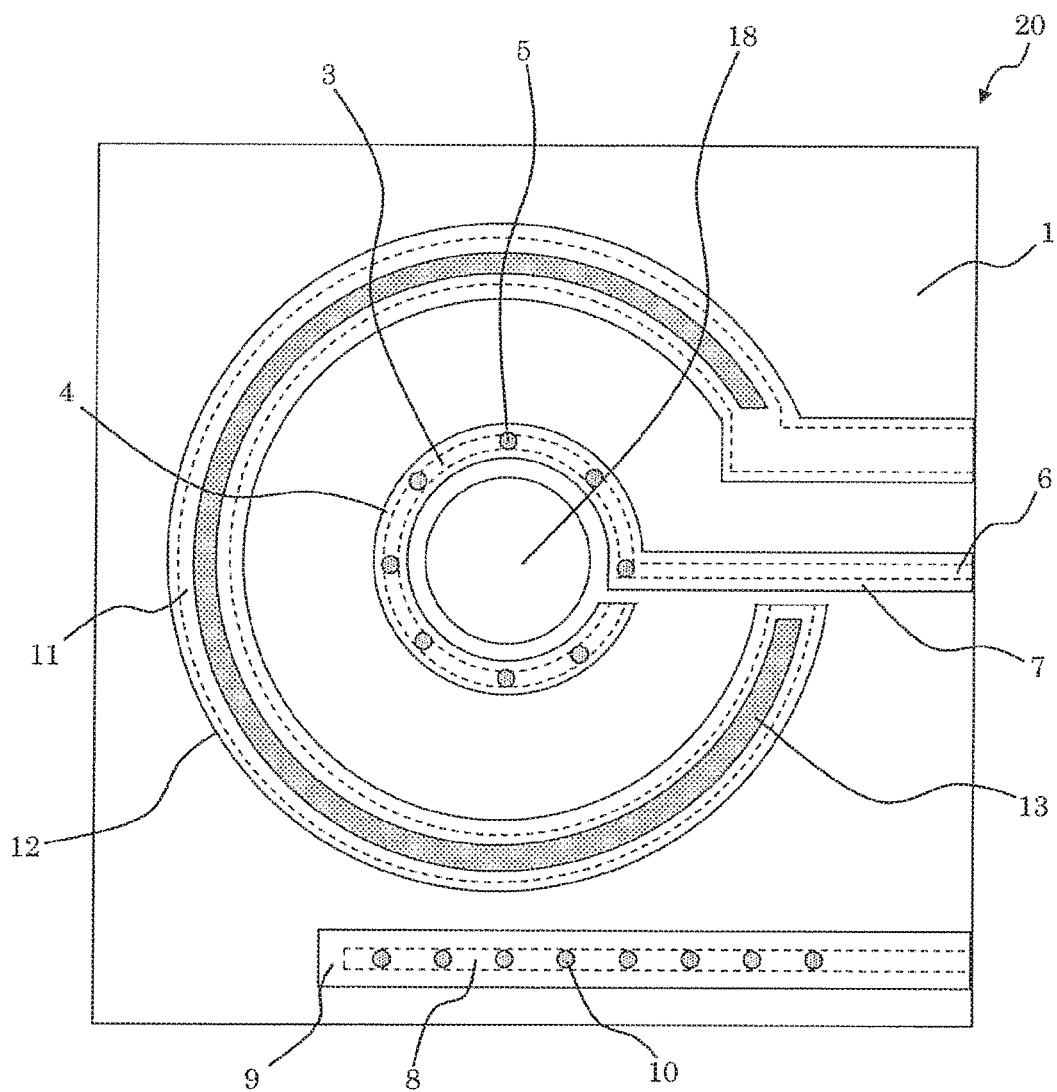
FIG. 5 is a top view of another example of an electrochemical measurement device for a biological specimen in Embodiment 1.

It should be noted that, in specimen placement portion 18, wall face 18A of specimen placement portion 18 preferably has a tapered shape which forms an angle that is greater than 90 degrees and less than 180 degrees with respect to bottom face 18B of specimen placement portion 18, as illustrated in FIG. 3, so that the biological specimen can be securely held. Furthermore, in order to be able to securely hold the biological specimen, specimen placement portion 18 may be a cone-shaped or polygonal pyramid-shaped hole, as illustrated in FIG. 4.

First electrode 3 is formed on base 1 to surround specimen placement portion 18. First electrode 3 can be formed into, for example, an elliptic or circular ring shape or a polygonal shape, etc. First electrode 3 is preferably ring-shaped. In addition, first electrode 3 is preferably concentric about specimen placement portion 18. First electrode 3 is made of, for example, a noble metal such as platinum, gold, or silver. Furthermore, first electrode 3 may be made of a material that is commonly used as an electrode material in batteries, such as carbon, or lithium cobalt oxide. The material of first electrode 3 may be selected in consideration of the composition of the culture solution, the required voltage and current, etc., at the time of measurement. It should be noted that first electrode 3, though having a discontinuous configuration, may be fully connected.

First insulating layer 4 is provided on base 1 to cover first electrode 3. The thickness of first insulating layer 4 is, for example, 0.5 μm. First insulating layer 4 is made from silicon dioxide, silicon nitride, or an organic substance, etc., to be able to provide insulation between first electrode 3 and the culture solution.

First insulating layer 4 has openings over first electrode 3. As such, first electrode 3 has first electrode exposed portions 5 at the openings of first insulating layer 4. First electrode 3 comes into contact with the culture solution at first electrode exposed portions 5. The openings of first insulating layer 4 are formed, for example, in the shape of a circle, a polygon, etc. The diameter of first electrode exposed portions 5 is, for example, 5 μm.

By covering first electrode 3 using first insulating layer 4 and coming into contact with the culture solution only at first electrode exposed portions 5 in the above manner, noise can be reduced and electrochemical measurement can be performed accurately due to the reasons described below.

When performing electrochemical measurement without covering first electrode 3 using first insulating layer 4 and causing the entirety of first electrode 3 to come into contact with the culture solution, non-faradaic current, which becomes noise, increases with the increase in electrode area, and thus there are instances where accurate electrochemical measurement cannot be performed. Furthermore, for example, when measuring the dissolved oxygen in the culture solution accompanying the respiratory activity of a fertilized ovum, the oxygen consumption amount accompanying an electrochemical reaction increases with the increase in the electrode area. This affects the oxygen concentration in the vicinity of the fertilized ovum, and thus there are instances where respiratory activity measurement cannot be performed accurately.

Therefore, the area of first electrode exposed portions 5 is preferably less than or equal to 500 μm$^2$ to reduce non-faradaic current, which is measurement noise, and to reduce the effect that oxygen consumption accompanying an electrochemical reaction has on the oxygen concentration in the vicinity of the fertilized ovum.

In addition, wire 6 which is drawn from first electrode 3 is covered by insulating layer 7. By having such a configuration, detection of electrochemical reaction-produced current at unnecessary positions can be reduced. However, wire 6 need not be covered by insulating layer 7. In this case, wire 6 comes into contact with the culture solution.

Furthermore, in order to perform the measurement at a plurality of positions around the biological specimen, a plurality of first electrode exposed portions 5 are provided in first electrode 3. First electrode exposed portions 5 are preferably disposed at equal intervals. For example, when four first electrode exposed portions 5 are to be provided in first electrode 3, first electrode exposed portions 5 are preferably disposed at equal intervals of 90 degrees each with specimen placement portion 18 as the center. Furthermore, for example, when eight first electrode exposed portions 5 are to be provided in first electrode 3, first electrode exposed portions 5 are preferably disposed at equal intervals of 45 degrees each with specimen placement portion 18 as the center. Stated differently, first electrode exposed portions 5 are preferably disposed to have point symmetry about specimen placement portion 18.

First electrode exposed portions 5 form a diffusion layer in their respective vicinities. Here, a diffusion layer is a region in the vicinity of the surface of first electrode exposed portions 5 where the chemical species concentration distribution is uneven. When measuring the dissolved oxygen in the culture solution accompanying the respiratory activity of the fertilized ovum, the chemical species is oxygen. As such, each first electrode exposed portion 5 is preferably disposed in such a way that the diffusion layer that is formed does not affect the electrochemical measurement of another first electrode exposed portion 5. For example, the distance between two adjacent first electrode exposed portions 5, among the plurality of first electrode exposed portions 5, is preferably greater than or equal to 5 times the diameter of first electrode exposed portions 5. By having such a configuration, the effect that the diffusion layer formed by one first electrode exposed portions 5 has on the diffusion layer formed by an adjacent first electrode exposed portion 5 can be minimized. As a result, it is possible to accurately measure the current value change caused by the respiratory activity of the biological specimen. More preferably, the distance between two adjacent first electrode exposed portions 5, among the plurality of first electrode exposed portions 5, is greater than or equal to 6.5 times the diameter of first electrode exposed portions 5. By having such a configuration, the effect that the diffusion layer formed by one first electrode exposed portions 5 has on the diffusion layer formed by an adjacent first electrode exposed portion 5 can be nearly eliminated. Here, an adjacent positional relationship refers to, for example, a positional relationship that is closest in terms of distance.

It should be noted that the diameter of first electrode exposed portions 5 refers to the diameter of the smallest circle including first electrode exposed portion 5 therein. For example, when first electrode exposed portions 5 are circles, the diameter of first electrode exposed portions 5 is the diameter. Furthermore, when first electrode exposed portions 5 are rectangles, the diameter of first electrode exposed portions 5 is the length of a diagonal line.

Furthermore, first electrode exposed portions 5 are preferably arranged at positions that are substantially equidistant from the center of specimen placement portion 18. First electrode exposed portions 5 are electrically connected by first electrode 3. By providing a plurality of first electrode exposed portions 5 equidistantly from specimen placement portion 18, the physicochemical change of state in oxygen concentration, etc., in the surroundings of the biological specimen can be measured as the average or sum total of the current values, via first electrode 3. As such, even if there is a bias in the activity of the biological specimen, electrochemical measurement device 20 can measure an average oxygen concentration in the surroundings of the biological specimen by electrochemical measurement.

In order to measure a reference value that is unaffected by the activity of the biological specimen, electrochemical measurement device 20 may include blank electrode 8 provided on base 1. Blank base 8 is covered by insulating layer 9 having openings, and includes blank electrode exposed portions 10 having surfaces that are exposed from the openings. Insulating layer 9 is equivalent to a third insulating layer. Blank electrode 8 is made of the same material as first electrode 3. Blank electrode exposed portions 10 may be provided singly or in a plurality.

However, the total area of blank electrode exposed portions 10 is preferably the same as the total area of first electrode exposed portions 5. The number and size of blank electrode exposed portions 10 is, for example, the same as the number and the size of first electrode exposed portions 5. By having the same configuration for blank electrode exposed portions 10 and first electrode exposed portions 5, the reference value can be measured without having to make calculations. The diameter of blank electrode exposed portions 10 is, for example, 5 μm.

Furthermore, blank electrode exposed portions 10 are preferably disposed in such a way that the physicochemical change in the surroundings of the biological specimen does not affect the electrochemical reaction occurring at blank electrode exposed portions 10. For example, the distance between the edge of the closest blank electrode exposed portion 10 and the edge of specimen placement portion 18 is preferably greater than or equal to 400 µm.

Furthermore, blank electrode exposed portions 10 are preferably disposed in such a way that there is no overlapping among the diffusion layers formed by blank electrode exposed portions 10 or with the diffusion layers formed by first electrode exposed portions 5, and the electrochemical reaction occurring at the first electrode exposed portions 5 and blank electrode exposed portions 10 are not affected. For example, the shortest distance between the edge of blank electrode exposed portion 10 and the edge of first electrode exposed portion 5 is preferably greater than or equal to 5 times the diameter of first electrode exposed portions 5. More preferably, the shortest distance between the edge of blank electrode exposed portion 10 and the edge of first electrode exposed portion 5 is greater than or equal to 6.5 times the diameter of first electrode exposed portions 5. Furthermore, when there is a plurality of blank electrode exposed portions 10, the distance between each of the plurality of blank electrode exposed portions 10 and first electrode exposed portion 5 may satisfy the above-described relationships. It should be noted that when the diameter of blank electrode exposed portions 10 and the diameter of first electrode exposed portions 5 differ significantly, the shortest distance between the edge of blank electrode exposed portions 10 and the edge of first electrode exposed portions 5 may be greater than or equal to the sum of half of the diameter of first electrode exposed portion 5 and half the diameter of blank electrode exposed portion 10.

The distance between the edges of adjacent blank electrode exposed portions 10 is preferably greater than or equal to 5 times the diameter of blank electrode exposed portions 10. More preferably, the distance between the edges of adjacent blank electrode exposed portions 10 is greater than or equal to 6.5 times the diameter of blank electrode exposed portions 10.

It should be noted that the diameter of blank electrode exposed portions 10 refers to the diameter of the smallest circle including blank electrode exposed portions 10 therein. For example, when blank electrode exposed portions 10 are circles, the diameter of blank electrode exposed portions 10 is the diameter. Furthermore, when blank electrode exposed portions 10 are rectangles, the diameter of blank electrode exposed portions 10 is the length of a diagonal line.

Furthermore, in electrochemical measurement device 20, counter electrode 11 may be provided on base 1. Counter electrode 11 generates a reaction opposite to the electrochemical reaction at first electrode exposed portions 5 in order to sustainably generate the electrochemical reaction at first electrode exposed portions 5. In other words, counter electrode 11 is an electrode that forms a pair with the first electrode which is a working electrode. In electrochemical measurement device 20, counter electrode 11 is an electrode that forms a pair with first electrode exposed portions 5 which are working electrodes that cause electrochemical reaction of the target object. For example, when measuring the dissolved oxygen in the culture solution accompanying the respiratory activity of a fertilized ovum, counter electrode 11 supplies the electrons needed in the oxygen-reduction reaction of first electrode exposed portions 5, and thus causes an oxidation reaction.

Counter electrode 11 is covered by insulating layer 12 which has an opening. Counter electrode 11 has counter electrode exposed portion 13 having a surface which is exposed from the opening. Insulating layer 12 is equivalent to a fourth insulating layer. Counter electrode 11 is formed on base 1 to surround first electrode 3 and specimen placement portion 18. Counter electrode 11 can be formed into, for example, an elliptic or circular ring shape or a polygonal shape, etc. Counter electrode 11 is preferably ring-shaped. In addition, counter electrode 11 is preferably concentric about specimen placement portion 18. Counter electrode 11 is made of, for example, a noble metal such as platinum, gold, or silver. Furthermore, counter electrode 11 may be made of a material that is commonly used as an electrode material in batteries, such as carbon, or lithium cobalt oxide. The material of counter electrode 11 may be selected in consideration of the composition of the culture solution, the required voltage and current, etc., at the time of measurement. Moreover, insulating layer 12 need not be provided.

Furthermore, counter electrode exposed portion 13 is preferably disposed in such a way that the physicochemical change in the surroundings of the biological specimen does not affect the electrochemical reaction occurring at counter electrode exposed portion 13. For example, the distance between the edge of counter electrode exposed portion 13 and the edge of specimen placement portion 18 is preferably greater than or equal to 400 µm. Furthermore, counter electrode exposed portion 13 is preferably disposed in such a way that the diffusion layer formed by counter electrode exposed portion 13 does not overlap with the diffusion layers formed by respective electrode exposed portions 5 and 10 and affect the electrochemical reactions occurring at electrode exposed portions 5 and 10. For example, the distance between the edge of counter electrode exposed portion 13 and the edges of electrode exposed portions 5 and 10 is preferably greater than or equal to 400 µm. Furthermore, the area of counter electrode exposed portion 13 is preferably greater than or equal to the total area of first electrode exposed portions 5. In the same manner, the area of counter electrode exposed portion 13 is preferably greater than or equal to the total area of blank electrode exposed portions 10.

Counter electrode 11 need not necessarily be formed on base 1. When not provided on base 1, measurement may be performed by inserting, as counter electrode 11, a bulk body made of a noble metal such as platinum, gold, or silver, or a material that is commonly used as an electrode material in batteries such as carbon or lithium cobalt oxide, into the culture solution. Furthermore, counter electrode 11 is not necessarily required, and need not be present.

It should be noted that first insulating layer 4, insulating layer 9 on blank electrode 8, and insulating layer 12 on counter electrode 11 may be configured of the same insulating layer. In other words, an insulator may be provided between first electrode 3, blank electrode 8, and counter electrode 11. In this manner, configuring using the same insulating layer enables the number of stages in the fabrication process to be reduced.

A reference electrode (reference electrode 17 in FIG. 6) is inserted into the culture solution. The material of the reference electrode uses platinum or gold, etc. Furthermore, a material including silver and silver chloride may be used as another material of the reference electrode. Furthermore, the reference electrode is preferably disposed in such a way that the diffusion layer formed by the reference electrode does not overlap with the diffusion layers formed by respective electrode exposed portions 5, 10, and 13 and affect the electrochemical reactions occurring at electrode exposed portions 5, 10, and 13. For example, the distance between the edge of reference electrode and the edges of electrode exposed portions 5, 10, and 13 is, for example, greater than or equal to 400 μm. It should be noted that the reference electrode may be formed on base 1.

First electrode 3 and blank electrode 8 are separately connected to a measurement amplifier. The potential difference between first electrode 3 and the reference electrode and blank electrode 8 and the reference electrode are measured separately, and the electrochemical reaction-produced current detected in first electrode 3 and in blank electrode 8 are measured separately.

It should be noted that when base 1 is a conductor or semiconductor, it is preferable that an insulating layer (not illustrated) be provided between base 1 and first electrode 3. Furthermore, when counter electrode 11 or the reference electrode is disposed on base 1, it is preferable that an insulating layer be provided between base 1 and counter electrode 11 or the reference electrode. The insulating layer is made from silicon dioxide, silicon nitride, or an organic substance, etc.

Furthermore, the outer circumference or periphery of base 1 may be surrounded by a wall. By forming a wall, a well is formed inside the wall. The wall is formed of, for example, glass, resin, silicon, ceramics, or silicone rubber, etc.

Figure 6:
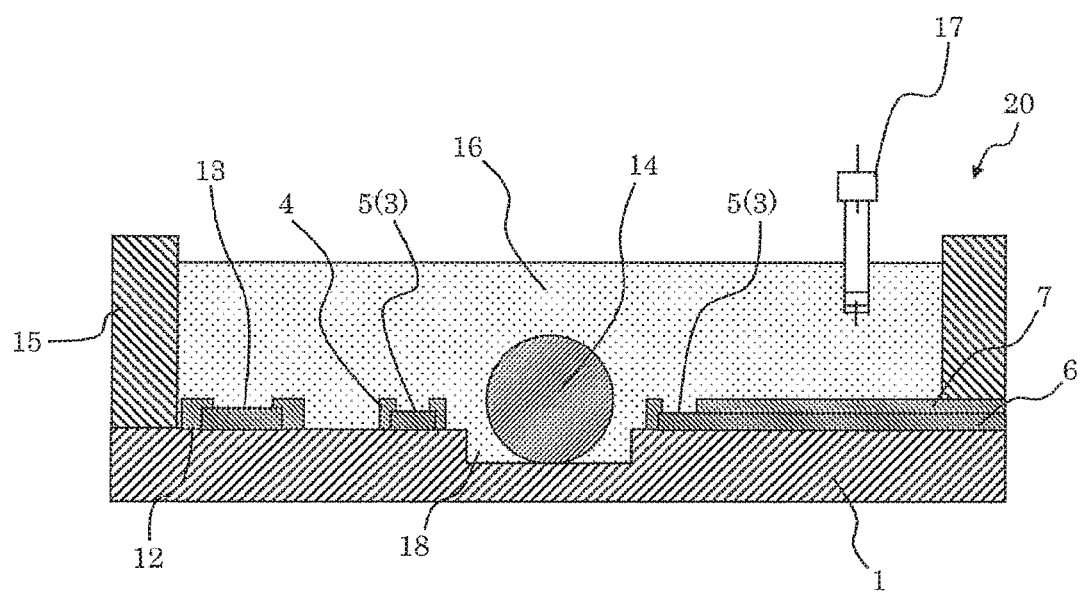
FIG. 6 is a cross-sectional view schematically illustrating the operation of an electrochemical measurement device for a biological specimen in Embodiment 1.

Next, the operation of electrochemical measurement device 20 for a biological specimen is described. FIG. 6 is a cross-sectional view schematically illustrating the operation of electrochemical measurement device 20 for a biological specimen in this embodiment.

The biological specimen is, for example, a cell, tissue, a fertilized ovum, etc. Active oxygen, metabolites, etc., from the biological specimen form a radial concentration gradient. Here, biological specimen 14 is described as a fertilized ovum.

Wall 15 is provided in the periphery of electrochemical measurement device 20. As such, well 16, into which the culture solution is introduced, is formed in the region enclosed by base 1 and wall 15.

First, the culture solution including the fertilized ovum is poured into well 16 to place the fertilized ovum on specimen placement portion 18.

Subsequently, reference electrode 17 is inserted into the culture solution. When reference electrode 17 is provided on base 1, insertion is not necessary. Furthermore, when counter electrode 11 is not provided on base 1, a counter electrode is inserted into the culture solution.

Then, with the potential of reference electrode 17 as a reference, a potential is applied to first electrode 3, and the value of the current that is produced by the electrochemical reaction and detected at first electrode 3 is measured. In the vicinity of first electrode exposed portions 5, reduction reaction of oxygen in the culture solution occurs. The amount of oxygen that is reduced in the vicinity of first electrode exposed portions 5 changes according to the amount of oxygen in the culture solution. Then, current, which is in accordance with the oxygen reduction reaction, flows in first electrode 3. Therefore, by measuring the amount of current, the amount of dissolved oxygen in the culture solution can be measured. The amount of dissolved oxygen is related to the amount of oxygen consumed as a result of activity by biological specimen 14 such as a fertilized ovum. As such, by measuring the amount of dissolved oxygen, the activity state of biological specimen 14 such as a fertilized ovum can be known. Furthermore, when measuring the current flowing in first electrode 3, which is a working electrode, an inverse potential to the potential of the working electrode is applied to counter electrode 11 in order to supply electrons necessary for the oxygen reduction reaction in first electrode exposed portions 5. In this manner, by supplying electrons from counter electrode 11, electrochemical measurement device 20 is capable of supporting the oxygen reduction reaction in first electrode exposed portions 5, and performing continued measurement. It should be noted that counter electrode 11 is not necessarily required, and thus need not be inserted into the culture solution.

Furthermore, blank electrode 8 is used for measuring a reference value of dissolved oxygen in the culture solution, that is unaffected by the biological specimen. A potential that is the same as the potential of the first electrode is applied to blank electrode 8, and the value of the current that flows is measured. The reference value measurement using blank electrode 8 is performed before or after, or simultaneously with the measurement using first electrode 3. It should be noted that blank electrode 8 need not be provided. In this case, the reference value can be measured by applying potential to first electrode 3 in a state where the biological specimen is not present, and measuring the current.

Embodiment 2

Hereinafter, an electrochemical measurement device for a biological specimen in Embodiment 2 will be described with reference to the drawings. In Embodiment 2, components identical with those in Embodiment 1 are assigned the same reference signs, and their detailed description is omitted.

Figure 7:
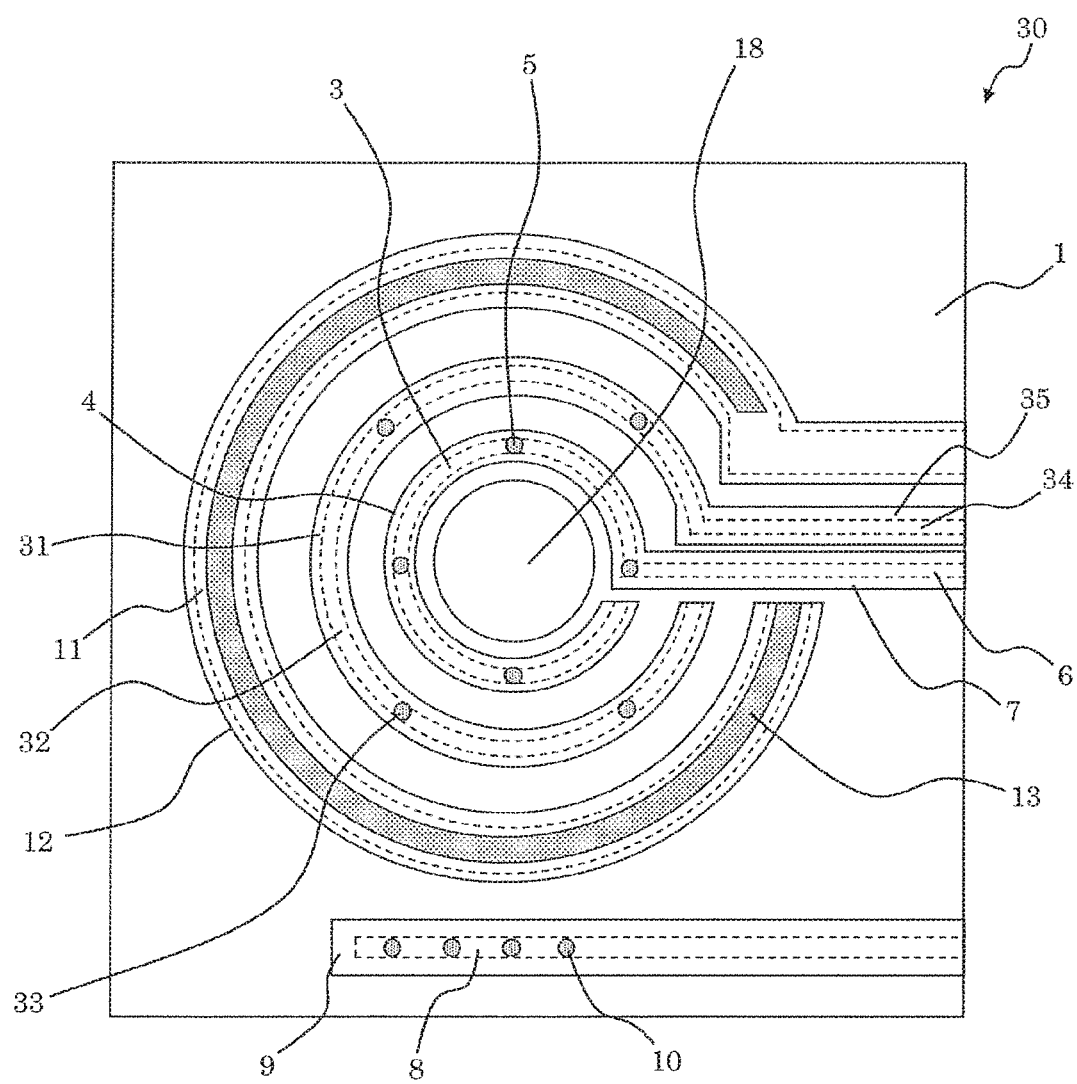
FIG. 7 is a top view of an electrochemical measurement device for a biological specimen in Embodiment 2.

FIG. 7 is a top view of electrochemical measurement device 30 for a biological specimen in this embodiment.

The point of difference between Embodiment 2 and Embodiment 1 is that second electrode 32 covered by second insulating layer 31 is provided on base 1 of electrochemical measurement device 30 for a biological specimen, to surround first electrode 3. As such, the distance between second electrode exposed portions 33 and specimen placement portion 18 is greater than the distance between first electrode exposed portions 5 and specimen placement portions 18.

In this manner, providing second electrode 32 outward of first electrode 32 enables electrochemical measurement of the biological specimen at a different distance from specimen placement portion 18. As such, biological specimen activity status monitoring that is dependent on the distance from the biological specimen can be performed.

Second electrode 32 can be formed into, for example, an elliptic or circular ring shape or a polygonal shape, etc. Second electrode 32 is preferably ring-shaped. In addition, second electrode 32 is preferably concentric about specimen placement portion 18.

Second electrode 32 can be made of the same material as first electrode 3. Second electrode 32 is made of, for example, a noble metal such as platinum, gold, or silver. Furthermore, second electrode 32 may be made of a material that is commonly used as an electrode material in batteries, such as carbon, or lithium cobalt oxide. The material of second electrode 32 may be selected in consideration of the composition of the culture solution, the required voltage and current, etc., at the time of measurement.

Second electrode 32 is covered by second insulating layer 31. The thickness of second insulating layer 31 is, for example, 0.5 μm. Second insulating layer 31 is made from silicon dioxide, silicon nitride, or an organic substance, etc., to be able to provide insulation between second electrode 32 and the culture solution.

Furthermore, second insulating layer 31 has openings over second electrode 32. As such, second electrode 32 has second electrode exposed portions 33 at the openings of second insulating layer 31. Second electrode 32 comes into contact with the culture solution at second electrode exposed portions 33. The openings of second insulating layer 31 are formed, for example, in the shape of a circle, a polygon, etc. The diameter of second electrode exposed portions 33 is, for example, 5 μm.

By covering second electrode 32 using second insulating layer 31 and coming into contact with the culture solution only at second electrode exposed portions 33 in the above manner, noise can be reduced and electrochemical measurement can be performed accurately due to the reasons described below.

When performing electrochemical measurement without covering second electrode 32 using second insulating layer 31 and causing the entirety of second electrode 32 to come into contact with the culture solution, non-faradaic current, which becomes noise, increases with the increase in electrode area, and thus there are instances where accurate electrochemical measurement cannot be performed. Furthermore, for example, when measuring the dissolved oxygen in the culture solution accompanying the respiratory activity of a fertilized ovum, the oxygen consumption amount accompanying an electrochemical reaction increases with the increase in the electrode area. This affects the oxygen concentration in the vicinity of the fertilized ovum, and thus there are instances where respiratory activity measurement cannot be performed accurately.

Therefore, the area of second electrode exposed portions 33 is preferably less than or equal to 500 μm$^2$ to reduce non-faradaic current, which is measurement noise, and to reduce the effect that oxygen consumption accompanying an electrochemical reaction has on the oxygen concentration in the vicinity of the fertilized ovum.

In addition, wire 34 which is drawn from second electrode 32 is covered by insulating layer 35. By having such a configuration, detection of electrochemical reaction-produced current at unintended positions can be reduced. However, wire 34 need not be covered by insulating layer 35. In this case, wire 34 comes into contact with the culture solution.

It should be noted that first insulating layer 4 covering first electrode 3 and second insulating layer 31 covering second electrode 32 may be formed using the same insulating layer. By forming using a single layer of the same insulating layer, the number of stages in the fabrication process can be reduced.

Furthermore, in order to perform the measurement at a plurality of positions around the biological specimen, a plurality of second electrode exposed portions 33 are preferably provided in second electrode 32. Second electrode exposed portions 33 are preferably disposed at equal intervals. For example, when four second electrode exposed portions 33 are to be provided in second electrode 32, second electrode exposed portions 33 are preferably disposed at equal intervals of 90 degrees each with specimen placement portion 18 as the center. For example, when eight second electrode exposed portions 33 are to be provided in second electrode 32, second electrode exposed portions 33 are preferably disposed at equal intervals of 45 degrees each with specimen placement portion 18 as the center.

Second electrode exposed portions 33 form a diffusion layer in their respective vicinities. As such, each second electrode exposed portion 33 is preferably disposed in such a way that the diffusion layer that is formed does not affect the electrochemical measurement of first electrode exposed portions 5 and another second electrode exposed portion 33. For example, the distance between each second electrode exposed portion 33 and an adjacent first electrode exposed portion 5 or second electrode exposed portion 33 is preferably greater than or equal to 5 times the diameter of second electrode exposed portions 33. Here, an adjacent positional relationship refers to, for example, a positional relationship that is closest in terms of distance.

By having such a configuration, the effect that the diffusion layer formed by one second electrode exposed portion 33 has on the diffusion layer formed by an adjacent first electrode exposed portions 5 or second electrode exposed portion 33 can be minimized. As a result, it is possible to accurately measure the current value change caused by the respiratory activity of the biological specimen. More preferably, the distance between each second electrode exposed portion 33 and an adjacent first electrode exposed portion 5 or second electrode exposed portion 33 is greater than or equal to 6.5 times the diameter of second electrode exposed portions 33. By having such a configuration, the effect that the diffusion layer formed by one second electrode exposed portion 33 has on the diffusion layer formed by an adjacent second electrode exposed portion 33 can be nearly eliminated.

Furthermore, each second electrode exposed portion 33 of second electrode 32 is preferably provided to be between two adjacent first electrode exposed portions 5 of first electrode 3 when seen from specimen placement portion 18. In other words, each second electrode exposed portion 33 is preferably provided on a different one of lines each of which connects the center of specimen placement portion 18 and the midpoint between a different pair of adjacent first electrode exposed portions 5. With this configuration, first electrode exposed portions 5 and second electrode exposed portions 33 can be maximally separated in the state where first electrode 3 and second electrode 3 are at the closest distance.

It should be noted that each second electrode exposed portion 33 of second electrode 32 is preferably disposed away from blank electrode exposed portions 10 by a distance greater than or equal to 6.5 times the sum of half the diameter of second electrode exposed portions 33 and half the diameter of blank electrode exposed portions 10, and disposed away from counter electrode exposed portions 13 and the reference electrode by a distance greater than or equal to 400 μm. Here, the diameter of second electrode exposed portions 33 refers to the diameter of the smallest circle including second electrode exposed portion 33 therein. For example, when second electrode exposed portions 33 are circles, the diameter of second electrode exposed portions 33 is the diameter. Furthermore, when second electrode exposed portions 33 are rectangles, the diameter of second electrode exposed portions 33 is the length of a diagonal line.

Furthermore, second electrode exposed portions 33 are preferably arranged at positions that are substantially equidistant from the center of specimen placement portion 18. Second electrode exposed portions 33 are electrically connected by second electrode 32. By providing a plurality of second electrode exposed portions 33 equidistantly from specimen placement portion 18, the physicochemical change of state in oxygen concentration, etc., in the surroundings of the biological specimen can be measured as the average or sum total of the current values, via second electrode 32. As such, even if there is a bias in the activity of the biological specimen, electrochemical measurement device 30 can measure an average oxygen concentration in the surroundings by electrochemical measurement.

The number and total area of second electrode exposed portions 33 of second electrode 32 is preferably the same as the number and total area of first electrode exposed portions 5 of first electrode 3.

The respective areas of first electrode exposed portions 5 are of the same size. The respective areas of second electrode exposed portions 33 are of the same size. In addition the area of one first electrode exposed portion 5 is the same as the area of one second electrode exposed portion 33.

It should be noted that second electrode 32, though having a discontinuous configuration, may be fully connected. However, when wire 6 of first electrode 3 is provided on the surface of base 1, it is preferable that second electrode 32 has discontinuous configuration. In this case, wire 6 of first electrode 3 can be provided in the part where second electrode 32 is disconnected. In the same manner, counter electrode 11 can also have a discontinuous configuration.

It should be noted that a single or a plurality of electrodes may be further provided outward of second electrode 32. By providing electrode exposed portions at different distances from specimen placement portion 18, it is possible to perform more detailed electrochemical measurement based on distance from the biological specimen.

Each of first electrode 3 and second electrode 32 is connected to a measurement amplifier, thus their respective currents can be measured simultaneously. Accordingly, the amount of dissolved oxygen, etc., which is a physicochemical change occurring in the surroundings of the biological specimen can be measured simultaneously. Furthermore, first electrode 3 and second electrode 32 may be connected to a single measurement amplifier using a switch, a relay, etc., and measurement can be performed by dividing the time (time division). By connecting a plurality of electrodes to a single measurement amplifier using a switching circuit including a switch, a relay, etc., the device can be simplified. However, when a switching circuit is used, it is preferable that the switch, relay, etc., operate at high-speed. By using a switch, etc., that operates at high-speed, makes it possible to accurately electrochemically measure the surroundings of the biological specimen for temporal change in the amount of dissolved oxygen, etc.

The electrochemical measurement device for a biological specimen according to the present disclosure includes a plurality of first electrode exposed portions disposed at positions that are equidistant from the specimen placement portion. By having such a configuration, it is possible to detect the total value of the physicochemical change of states of, for example, oxygen concentration, in a plurality of directions in the vicinity of the biological specimen, and thus an average physicochemical change of states in the surroundings of the biological specimen can be measured.

Since the first electrode exposed portions are exposed portions of the first electrode that is covered by the first insulating layer, the plurality of first electrode exposed portions are electrically connected by way of the first electrode. As such, the total value of the physicochemical change of state of, for example, oxygen concentration, etc., of the biological specimen in a plurality of directions can be obtained from a single wire.

Furthermore, the electrochemical measurement device includes a plurality of second electrodes outward of the first electrode. By having such a configuration, the concentration gradient of the amount of dissolved oxygen can be measured from the current detected at the first electrode or the second electrodes which have different distances from the biological specimen. As a result, physicochemical change obtained by spatially dividing the surroundings of the biological specimen can be easily measured.

It should be noted that, in the present disclosure, terms indicating directions, such as top face, indicate relative directions dependent only on the relative positional relationship of structural components of the electrochemical measurement device, and do not indicate absolute directions such as vertical direction, etc.

Although an electrochemical measurement device according to one or more aspects has been described on the basis of the foregoing embodiments, the present disclosure is not limited to these embodiments. Forms obtained by various modifications to the exemplary embodiments that can be conceived by a person of skill in the art as well as forms realized by combining structural components in different exemplary embodiments, which are within the scope of the essence of the present disclosure, may be included in one or more aspects.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The present disclosure can be used in an electrochemical measurement device, etc., which electrochemically measures the activity state of a biological specimen such as a cell, such as a fertilized ovum, tissue, etc.

What is claimed is:

1. An electrochemical measurement device, comprising:
   a base;
   a specimen placement portion disposed on the base, for placing a biological specimen;
   a first electrode disposed on the base and surrounding the specimen placement portion; and
   a first insulating layer covering the first electrode, wherein:
   the first insulating layer has a plurality of openings,
   the first electrode has a plurality of first electrode exposed portions which are portions of the first electrode that are exposed from the plurality of openings of the first insulating layer,
   an area of each of the first electrode exposed portions is less than or equal to 500 $\mu m^2$,
   a distance between each of the first electrode exposed portions and a center of the specimen placement portion is greater than 100 $\mu m$, and
   the plurality of first electrode exposed portions are arranged on a perimeter of a circle surrounding the specimen placement portion.

2. The electrochemical measurement device according to claim 1,
   wherein the plurality of first electrode exposed portions are disposed at positions that are substantially equidistant from the specimen placement portion.

3. The electrochemical measurement device according to claim 1,
   wherein the plurality of first electrode exposed portions are disposed at equal intervals.

4. The electrochemical measurement device according to claim 1,
   wherein the first electrode is ring-shaped.

5. The electrochemical measurement device according to claim 1,
wherein a distance between two adjacent first electrode exposed portions among the plurality of first electrode exposed portions is greater than or equal to five times a diameter of one of the two adjacent first electrode exposed portions.

6. The electrochemical measurement device according to claim 1, comprising:
a second electrode disposed on the base and surrounding the first electrode; and
a second insulating layer covering the second electrode,
wherein the second insulating layer has a plurality of openings, and
the second electrode has a plurality of second electrode exposed portions which are portions of the second electrode that are exposed from the plurality of openings of the second insulating layer.

7. The electrochemical measurement device according to claim 6,
wherein the plurality of second electrode exposed portions are disposed at positions that are substantially equidistant from the specimen placement portion.

8. The electrochemical measurement device according to claim 6,
wherein the plurality of second electrode exposed portions are disposed at equal intervals.

9. The electrochemical measurement device according to claim 6,
wherein each of the plurality of second electrode exposed portions is disposed on a different one of lines each of which connects a center of the specimen placement portion and a midpoint between a different pair of adjacent first electrode exposed portions among the plurality of first electrode exposed portions.

10. The electrochemical measurement device according to claim 6,
wherein the second electrode is ring-shaped.

11. The electrochemical measurement device according to claim 6,
wherein a distance between two adjacent first electrode exposed portions among the plurality of first electrode exposed portions is greater than or equal to five times a diameter of one of the two adjacent first electrode exposed portions,
a distance between two adjacent second electrode exposed portions among the plurality of second electrode exposed portions is greater than or equal to five times a diameter of one of the two adjacent second electrode exposed portions, and
a distance between a closest first electrode exposed portion and second electrode exposed portion among the plurality of first electrode exposed portions and the plurality of second electrode exposed portions is greater than or equal to five times a diameter of one of the plurality of second electrode exposed portions.

12. The electrochemical measurement device according to claim 1,
wherein the specimen placement portion is a bottomed hole having one of a columnar shape and a conical shape.

13. The electrochemical measurement device according to claim 1, further comprising:
a blank electrode disposed on the base, for measuring a reference value that is unaffected by activity of the biological specimen; and
a third insulating layer covering the blank electrode,
wherein the third insulating layer has a plurality of openings, and
the blank electrode has a plurality of blank electrode exposed portions which are portions of the blank electrode that are exposed from the plurality of openings of the third insulating layer.

14. The electrochemical measurement device according to claim 13,
wherein the plurality of blank electrode exposed portions have a total area that is same as a total area of the plurality of first electrode exposed portions, and
each of the plurality of blank electrode exposed portions is disposed at a position that is separated from a first electrode exposed portion that is closest to the blank electrode exposed portion among the plurality of the first electrode exposed portions, by a distance greater than or equal to five times a diameter of the first electrode exposed portion.

15. The electrochemical measurement device according to claim 1, further comprising
a counter electrode disposed on the base and paired with the first electrode,
wherein the counter electrode has a counter electrode exposed portion having an exposed surface,
the counter electrode exposed portion has an area that is greater than a total area of the plurality of the first electrode exposed portions, and
the counter electrode exposed portion is disposed at a position that is separated from each of the plurality of the first electrode exposed portions by a distance greater than or equal to 400 μm.

16. The electrochemical measurement device according to claim 15, further comprising
a fourth insulating layer covering the counter electrode,
wherein the fourth insulating layer has an opening, and
the counter electrode exposed portion is exposed from the opening of the fourth insulating layer.

17. The electrochemical measurement device according to claim 13,
wherein the biological specimen to be measured is a fertilized ovum, and
each of the plurality of blank electrode exposed portions is disposed at a position that is separated from the specimen placement portion by a distance greater than or equal to 400 μm.

18. The electrochemical measurement device according to claim 15,
wherein the biological specimen to be measured is a fertilized ovum, and
the counter electrode exposed portion is disposed at a position that is separated from the specimen placement portion by a distance greater than or equal to 400 μm.

19. An electrochemical measurement device, comprising:
a base;
a specimen placement portion disposed on the base, for placing a biological specimen;
a first electrode disposed on the base and surrounding the specimen placement portion; and
a first insulating layer covering the first electrode, wherein:
the first insulating layer has a plurality of openings,
the first electrode has a plurality of first electrode exposed portions which are portions of the first electrode that are exposed from the plurality of openings of the first insulating layer, and a distance between two adjacent first electrode exposed portions among the plurality of first electrode exposed portions is greater than or equal to five times a diameter of one of the two adjacent first electrode exposed portions.

20. An electrochemical measurement device, comprising:
a base;
a specimen placement portion disposed on the base, for placing a biological specimen;
a first electrode disposed on the base and surrounding the specimen placement portion;
a first insulating layer covering the first electrode; and
a counter electrode disposed on the base and paired with the first electrode, wherein:
the first insulating layer has a plurality of openings,
the first electrode has a plurality of first electrode exposed portions which are portions of the first electrode that are exposed from the plurality of openings of the first insulating layer,
the counter electrode has a counter electrode exposed portion having an exposed surface,
the counter electrode exposed portion has an area that is greater than a total area of the plurality of the first electrode exposed portions, and
the counter electrode exposed portion is disposed at a position that is separated from each of the plurality of the first electrode exposed portions by a distance greater than or equal to 400 μm.

* * * * *